US009095564B2

(12) United States Patent
Dickneite et al.

(10) Patent No.: US 9,095,564 B2
(45) Date of Patent: *Aug. 4, 2015

(54) VON WILLEBRAND FACTOR OR FACTOR VIII AND VON WILLEBRAND FACTOR FOR THE TREATMENT OF COAGULOPATHY INDUCED BY INHIBITORS OF THROMBOCYTES

(71) Applicant: CSL Behring GmbH, Marburg (DE)

(72) Inventors: Gerhard Dickneite, Marburg (DE); Ingo Pragst, Marburg (DE); Henrique Lessa, Cologne (DE); Thorsten Haas, Oberperfuss (AT); Stefan Zeitler, Reifenthal (DE)

(73) Assignee: CSL Behring GmbH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/071,193

(22) Filed: Nov. 4, 2013

(65) Prior Publication Data

US 2014/0128325 A1 May 8, 2014

Related U.S. Application Data

(63) Continuation of application No. 13/003,139, filed as application No. PCT/EP2009/005027 on Jul. 10, 2009, now Pat. No. 8,603,979.

(30) Foreign Application Priority Data

Jul. 10, 2008 (DE) .......................... 10 2008 032 361

(51) Int. Cl.
*A61K 38/37* (2006.01)
*C07K 14/755* (2006.01)
*A61K 38/36* (2006.01)

(52) U.S. Cl.
CPC .................. *A61K 38/36* (2013.01); *A61K 38/37* (2013.01)

(58) Field of Classification Search
CPC .... A61K 38/36; A61K 38/37; A61K 2300/00
See application file for complete search history.

(56) References Cited

U.S. PATENT DOCUMENTS

| | | | |
|---|---|---|---|
| 5,571,784 A | 11/1996 | Reers et al. | |
| 8,603,979 B2 * | 12/2013 | Dickneite et al. | 514/14.1 |
| 2002/0062492 A1 | 5/2002 | Lubon et al. | |
| 2003/0125250 A1 | 7/2003 | Araki et al. | |
| 2003/0212042 A1 | 11/2003 | Lassila et al. | |

FOREIGN PATENT DOCUMENTS

| | | |
|---|---|---|
| CA | 2156991 | 2/1996 |
| DE | 44 30 205 A1 | 2/1996 |
| EP | 0 713 881 A2 | 5/1996 |
| WO | WO 97/29753 A1 | 8/1997 |

OTHER PUBLICATIONS

Wang et al. The Effect of Preoperative Clopidogrel on Bleeding After Coronary Artery Bypass Surgery. Journal of Surgical Education, Mar./Apr. 2007. vol. 64, No. 2, pp. 89-92.*
Bertrand et al. Double-Blind Study of the Safety of Clopidogrel With and Without a Loading Dose in Combination With Aspirin Compared with Ticlopidine in Combination With Aspirin After Coronary Stenting: The Clopidogrel Aspirin Stent International Cooperative Study (CLASSICS). Circulation, 2000. vol. 102, pp. 624-629.*
Auerswald et al. The role of plasma-derived factor VII/von Willebrand factor concentrates in the treatment of hemophilia A patients. Hematologica, 2003. 2 pages.*
Alevriadou BR, Moake JL, Turner NA, Ruggeri ZM, Folie BJ, Phillips MD, Schreiber AB, Hrinda ME, McIntire IV, 1993, Blood 81, 1263-1276M.
Australian Office Action for Australian Patent Application No. 2009268289, dated Jul. 18, 2013, 5 pages.
Berntorp, E, et al.: "A systematic overview of the first pasteurised VWF/FVIII medicinal product, Haemate® P/Humate® -P: History and clinical performance" European Journal of Haematology, Suppl. 70, ISSN 0902-4441 (May 2008), pp. 3-35.
Born et al., "Antiplatelet Drugs," British Journal of Pharmacology, 147:S241-S251 (2006).
CSL Behring GmbH: Haemate® P—Producktmonografie. *Biotherapies for Life*, Marburg, Feb. 2007. pp. 1-40—Firmensschrift.
CSL Behring Gmbh, "Summary of Product Characteristics," Haemate P 500 Powder and solvent for solution for injection or infusion, revised Mar. 21, 2013, 15 pages.
Dickneite G, Friesen H.-J., Kumpe G, Reers M, 1996 Platelets 7, 283-290.
Dickneite G, Nicolay U, Friesen H.-J., Reers M, 1998 Thromb Haemost 80, 192-8.
Dickneite G, Doerr B, Kaspereit F, 2008 Anesth Analg 106, 1070-7.
Elg, M et al.: "Effects of Agents, Used to Treat Bleeding Disorders, on Bleeding Time Prolonged by a Very High Dose of a Direct Thrombin Inhibitor in Anesthesized Rats and Rabbits" Thrombosis Research, vol. 101, ISSN: 0049-3848 (Jan. 2001) pp. 159-170.
European Application No. 09777111.7: Communication of a notice of opposition, dated Jun. 28, 2013, 1 page.
European Application No. 09777111.7: Notice of opposition to a European Patent, dated Jun. 18, 2013, 38 pages.

(Continued)

*Primary Examiner* — Marcela M Cordero Garcia
(74) *Attorney, Agent, or Firm* — Finnegan, Henderson, Farabow, Garrett & Dunner, LLP

(57) ABSTRACT

The present invention relates to a von Willebrand Factor for use in the treatment and/or prevention of a bleeding event associated with a thrombopathy induced by substances inhibiting thrombocytes. Furthermore, the present invention relates to a method of treating and/or preventing a disorder related to a bleeding event associated with a thrombopathy induced by substances inhibiting thrombocytes comprising administering a pharmaceutically effective amount of a von-Willebrand-Factor (vWF) to a patient in need thereof. The present invention also relates to a composition comprising vWF and a composition comprising FVIII for simultaneous, separate or sequential use for use in the treatment and/or prevention of a bleeding event associated with a thrombopathy induced by substances inhibiting thrombocytes.

20 Claims, 6 Drawing Sheets

(56) References Cited

OTHER PUBLICATIONS

"Gebrauchsinformation: Information für den Anwender. Wilfactin 1000 I.U./10 ml. Pulver und Lösungsmittel zur Herstellung einer Injektionslösung. Humanes Factor von Willebrand. [Package Leaflet: Information for the User—Wilfactin 1000 I.U./10ml. Powder and solvent for preparation of a solution for injection. Human von Willebrand factor]," [online]: http://bijsluiters.fagg-afmps.be, 10 pages (2011). English translation of p. 1.

German Office Action in Application No. 10 2008 032 361.6 dated Sep. 6, 2011.

Goudemand et al., "Pharmacokinetic studies on Wilfactin®, a von Willebrand factor concentrate with a low factor VII content treated with three virus-inactivation/removal methods," Journal of Thrombosis and Haemostasis, 3:2219-2227 (2005).

Gralnick HR, Williams S, McKeown L, Kramer W, Krutzsch H, Gorecki M, Pinet A Garfinkel Li, 1992 Proc. Natl. Acad. Sci. USA, 89, 7880-7884.

Hemker HC, and Poliwoda H, 1993, 1-18, Barthels M and Polidowa H, Thieme, Stuttgart, Germany.

International Search Report and Written Opinion for International Application No. PCT/EP2009/005027, dated Nov. 3, 2009, 13 pages.

Koscielny et al., "A Practical Concept for Preoperative Management of Patients With Impaired Primary Hemostasis," Clin. Appl. Thrombosis/Hemostasis, 10(2):155-166 (2004).

Koscielny et al., "Perioperatives Management von Patienten unter ASS/Clopidrogel-Medikation," Vascular Care, 14:28-43 (2008). English translation provided, 12 pages.

Lethagen, S. et al.: "New Bleeding Time Devices with Retractable Blades Evaluated in Children, Healthy Volunteers and Patients with Prolonged Bleeding Time" Thromb Haemost (Oct. 1993) 18;70(4): pp. 595-597.

Lethagen, S. et al., "von Willebrand factor/factor VIII concentrate (Haemate® P) dosing based on pharmacokinetics: a prospective multicenter trial in elective surgery", Journal of Thrombosis and Haemostatis, vol. 5, 2007, 1420-30.

Pock et al., "Biochemical comparison of VWF/FVIII concentrates. Are there differences in product characteristics and purity?," Hemophilia World Congress 2008. Octapharma. [online]: http://www.vonwillebrand.se/PageFiles/484/Biokemiska%20j%C3%A4mf%C3%B6relser%20mellan%20olika%20VWF-FVIII-koncentrat.pdf, 2008, 2 pages.

Plaimauer et al., "Recombinant von Willebrand Factor: Preclinical Development," Seminars in Thrombosis and Hemostasis, 27(4):395-403 (2001).

Ruggeri ZM, Seminars in Hematology, 1994, 31, 229-239.

Ruggeri ZM, 1993 Current Opinion in Cell Biology, 5, 898-906.

Tomokiyo et al., "Von Willebrand Factor Accelerates Platelet Adhesion and Thrombus Formation on a Collagen Surface in Platelet-reduced Blood Under Flow Conditions," Blood (2005) 105(3):1078-1084, The American Society of Hematology.

Written Confirmation by the German Central Library for Medicine of the registration date, 1 page (Mar. 27, 2013).

Matsumoto et al., "TTP and anti-platelet agents," Hematology and Oncology, 41(3):238-244 (2000).

Office Action for Japanese Patent Application No. 2011-517038 dated Apr. 1, 2014. (6 pages).

Dimichele et al., "Use of DDAVP in Inherited and Acquired Platelet Dysfunction," *American Journal of Hematology*, 33:39-45 (1990).

Fischer et al., "Structural analysis of recombinant von Willebrand factor produced at industrial scale fermentation of transformed CHO cells co-expressing recombinant furin," *FEBS Letters*, 375:259-262 (1995).

Mannucci et al., "Controlled Trial of Desmopressin in Liver Cirrhosis and Other Conditions Associated With a Prolonged Bleeding Time," *Blood*, 67(4):1148-1153 (1986).

Averkov O.V., "Clopidogrel in treatment of ischemic heart syndrome without persistent raise of segment ST in ECG. Lessons of Investigation CURE. Which is applicable in Russia?," J. Cardiovascular Therapy and Prevention, N.2, pp. 67-75 (2004). Machine translation provided.

Office Action for Russian Patent Application No. 2011104705/15(006622) dated Sep. 22, 2014, together with English translation (5 pages).

Shumakov V.A. et al., "Antithrombocytic therapy in patients suffering from CHD: clopidogrel and/or acetylsalicylic acid," J. New medicine of millennium, N.4, pp. 26-30 (2007). Machine translation provided.

* cited by examiner

VON WILLEBRAND FACTOR OR FACTOR VIII AND VON WILLEBRAND FACTOR FOR THE TREATMENT OF COAGULOPATHY INDUCED BY INHIBITORS OF THROMBOCYTES

This application is a continuation of U.S. application Ser. No. 13/003,139, which has a §371(c) date of Jan. 7, 2011 (now U.S. Pat. No. 8,603,979) and is a U.S. national stage entry of International Application No. PCT/EP2009/005027, filed Jul. 10, 2009, and claims the benefit of priority of German Application No. 10 2008 032 361.6, filed Jul. 10, 2008, all of which are incorporated herein by reference in their entirety.

The present invention relates to a von Willebrand Factor for use in the treatment and/or prevention of a bleeding event associated with a thrombopathy induced by substances inhibiting thrombocytes. Furthermore, the present invention relates to a method of treating and/or preventing a disorder related to a bleeding event associated with a thrombopathy induced by substances inhibiting thrombocytes comprising administering a pharmaceutically effective amount of a von-Willebrand-Factor (vWF) to a patient in need thereof. The present invention also relates to a composition comprising vWF and a composition comprising FVIII for simultaneous, separate or sequential use for use in the treatment and/or prevention of a bleeding event associated with a thrombopathy induced by substances inhibiting thrombocytes.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

An imbalance of the components of the coagulation or the fibrinolytic system will manifest clinically either in thrombosis or hemorrhage, respectively. Both pathological situations can be life-threatening. After a thrombotic event, e.g. during acute myocardial infarction, it will be tried to intervene into the actual lysis and coagulation balance. The fibrinolytic system will be supported e.g. by administration of Streptokinase (SK) or plasminogen activators (t-PA, uPA) to dissolve the existing blood clot. The thrombocyte activation is inhibited or reduced by thrombocyte inhibitors. Thereby the vessels closed by a thrombus will be recanalized and the formation of a new thrombus will be prevented. Inhibitors of the thrombocyte functions can act at different sites. Inhibitors of Cyclooxigenase (e.g. Acetylsalicylic acid) prevent the formation of Thromboxan $A_2$ ($TXA_2$) which is a potent activator of the thrombocyte function. Antagonists of ADP-receptors on the surface of thrombocytes (e.g. Clopidrogel, Ticlopidin) prevent the binding of the thrombocyte activator ADP to its receptor and prevent the activation of thrombocytes. The fibrinogen receptor on the thrombocyte surface, Glycoprotein IIb/IIIa (GP IIb/IIIa), induces the aggregation of thrombocytes after the binding of its agonist fibrinogen (or vWF). Monoclonal antibodies against GP IIb/IIIa (e.g. Abciximab) or receptor antagonists as Eptifibatide or Tirofiban also prevent the aggregation of thrombocytes.

On the other hand a certain potential to form a thrombus after a vessel lesion is necessary to prevent hemorrhage at these locations. The therapy of potentially evolving life threatening hemorrhage during the therapy with thrombocyte inhibitors includes discontinuation of this therapy and the administration of coagulation enhancers. Such coagulation enhancers consist, among others, of partially pre-activated coagulation factors as in the marketed product FEIBA® (Baxter) or the recombinant coagulation factor VIIa (NovoSeven®, Novo Nordisk). Primarily these coagulation enhancers result in a reduction of the therapeutic effects of the thrombocyte inhibition. Dickneite et al. (Dickneite G, Friesen H.- J., Kumpe G, Reers M, 1996 Platelets 7, 283-290, Dickneite G, Nicolay U, Friesen H.- J., Reers M, 1998 Thromb Haemost 80, 192-8) describe the use of vWF and Haemate® (CSL Behring) as a coagulation enhancer during a bleeding event induced by the recombinant thrombin inhibitor Hirudin.

A quantitative measure for the anti-coagulation and fibrinolytic effects in the clinic are different diagnostic procedures like the thromboelastography, the thrombin generation assay, the activated partial thromboplastin time (aPTT) or the prothrombin time (PT). A method to evaluate the prevention of severe hemorrhage in experimental settings is the bleeding of organs after a traumatic injury (Dickneite G, Doerr B, Kaspereit F, 2008 Anesth Analg 106, 1070-7).

According to mechanistic investigations regarding the occurrence of haemostasis after vessel lesion, thrombocytes will bind primarily to the subendothelial collagen fibers via the von Willebrand factor (vWF). vWF is the only factor with the capability to bind thrombocytes efficiently at low (e.g. in the venous area) as well as with high shear rates (e.g. in the arterial, coronary region or in plaque induced stenosis of vessels) by binding to exposed collagen (Ruggeri Z M, Seminars in Hematology, 1994, 31, 229-239). The following aggregation of thrombocytes and a subsequent retraction and contraction of the aggregated platelets by the action of thrombin induces a haemostatic plug during secondary heamostasis (Hemker H C, and Poliwoda H, 1993, 1-18, Barthels M and Polidowa H, Thieme, Stuttgart, Germany).

At present vWF is the largest known plasma protein. It is a multimeric glycoprotein with two biological properties. At local vessel injuries it mediates thrombocyte adhesion followed by thrombus formation and it acts as a carrier for the procoagulatory coagulation factor VIII (Ruggeri Z M, 1993 Current Opinion in Cell Biology, 5, 898-906). vWF is found in certain amounts in a factor VIII-free form in the subendothelial cells and will be stored in a factor VIII-free form in the α-granula of the thrombocytes. Thrombocytes have two receptors for vWF: first GP Ib in the GP Ib-IX-V complex and second GP IIb-IIIa (Ruggeri Z M, 1994 Seminars in Hematology 31, 229-239). Via its first receptor vWF induces a thrombocyte adhesion at the side of the vessel injury, which is followed by vWF and/or fibrinogen binding to the GP IIb/IIIa receptor and supports the subsequent aggregation of thrombocytes. According to this background it is discussed in the literature to use inhibitors for the binding of vWF as a principle for an anticoagulant drug (Alevriadou B R, Moake J L, Turner N A, Ruggeri Z M, Folie B J, Phillips M D, Schreiber A B, Hrinda M E, McIntire I V, 1993, Blood 81, 1263-1276M; Grainick H R, Williams S, McKeown L, Kramer W, Krutzsch H, Gorecki M, Pinet A Garfinkel L I, 1992 Proc. Natl. Acad. Sci. USA, 89, 7880-7884).

There is still a high medical need to diminish or prevent the adverse events of hemorrhage after the administration of thrombocyte inhibitors. Therefore the technical problem underlying the present invention is the provision of means and methods for successfully treating a bleeding event caused by the administration of substances inhibiting thrombocytes.

The solution to this technical problem is achieved by providing the embodiments characterised in the claims.

Surprisingly it is found that the adverse events of bleeding or hemorrhage during or after administering a substance inhibiting the thrombocytes were diminished after the administration of von Willebrand factor (vWF). Therefore a suitable supplementation with a vWF containing pharmaceutical composition will antagonise the adverse events of enhanced bleeding following the antithrombocytic therapy. The adverse effects resulting of the effects of anticoagulants or fibrinolytics therefore are diminished or prevented. To reduce the bleeding risk in patients the vWF can be administered either prophylactically or following the anti-thrombocytic treatment.

Accordingly, the present invention relates to a von-Willebrand-Factor (vWF) for treatment and/or prevention of a bleeding event associated with a coagulopathy, especially a thrombopathy, induced by substances inhibiting thrombocytes.

The term "thrombopathy" in accordance with the present invention relates to a dysfunction in the thrombocytes whereas the number of thrombocytes is normal or marginal changed. This can be seen as a distinguishing feature to thrombocytopenia, also known as thrombopenia, where relatively few platelets in blood are present. Regarding thrombopathy there exist a number of medicaments restricting the function(s) of thrombocytes, e.g. acetylsalicylic acid, diclofenac, heparin, penicillin and others. Thrombopathy is also known as thrombocytopathy which term is used herein as well.

In relation to the plasmatic coagulation, the thrombocytes have two important characteristics or functions: the adhesion to the subendothelium on the one hand and the aggregation among each other on the other hand. In accordance with the present invention the term "substances inhibiting thrombocytes" relates to substances inhibiting the aggregation of the thrombocytes. In general, theses substances are also known as thrombocyte-inhibitors or antiplatelet drugs or platelet aggregation inhibitors and are administered to patients to prevent the growth of thrombi especially in the arteries i.e. they are administered to prevent e.g. a stroke, a myocardial infaction or another related disease.

Therefore, according to the invention the term "thrombopathy, induced by substances inhibiting thrombocytes" relates to a dysfunction in the aggregation of the thrombocytes whereas the number of thrombocytes is normal or marginal changed. In contrast thrombocytopenia is related to a decrease of the number of thrombocytes. The thrombopathy is induced by one, two or more substances which inhibit the aggregation of thrombocytes. Preferably these substances will inhibit the cyclooxygenase and/or the ADP receptor.

The term "thrombopathy" as used herein preferably does not include hereditary diseases like a thrombasthenia caused by a deficiency of platelet membrane glycoproteins (GP) IIb/IIIa (Thrombasthenia Glanzmann) or Bernard-Soulier's syndrome caused by a deficiency of GP Ib. The thrombasthenia is an inherited abnormality of the blood platelets characterized especially by defective clot retraction and often by prolonged bleeding time.

The present invention further related to a method of treating and/or preventing a disorder related to a bleeding event associated with a thrombopathy induced by substances inhibiting thrombocytes comprising administering a pharmaceutically effective amount of a von-Willebrand-Factor (vWF) to a patient in need thereof.

In a preferred embodiment of the use of the von Willebrand Factor or the method of the invention the vWF is used or administered in combination with factor VIII as a factor VIII/von-Willebrand-factor (FVIII/vWF) combination.

Preferably, the vWF or the FVIII/vWF combination is formulated in a pharmaceutical composition, optionally comprising a pharmaceutically acceptable carrier, excipient and/or diluent.

The term "pharmaceutical composition" as used herein relates to a composition for administration to a patient, preferably a human patient. The pharmaceutical composition envisages alternatively mixtures of vWF or a combination of vWF and FVIII. In cases where more than one compound is comprised in the composition it is understood that none of these compounds has an inhibitory effect on the other compounds also comprised in the composition.

It is preferred that said pharmaceutical composition comprises a pharmaceutically acceptable carrier, excipient and/or diluent. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous or intramuscular administration. It is particularly preferred that said administration is carried out by injection and/or delivery, e.g., to a site in the bloodstream. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

The pharmaceutical composition according to the invention may be administered to the patient at a dose range of 10 to 1000 units vWF per kg body weight. Alternatively, if the FVIII/vWF combination is used the dose range administered is between 5 and 400 Units FVIII per kg body weight and between 10 and 1000 units vWF per kg body weight.

A preferred dose range will be between 30 and 500 units vWF per kg body weight or alternatively for the FVIII/vWF combination a dose of 20 to 200 Units FVIII and 30 to 500 units vWF per kg body weight will be administered.

As a pharmaceutical composition comprising vWF or vWF and FVIII, respectively, used according to the invention any marketed product comprising vWF or vWF and FVIII can be used, e.g. Haemate® P and Humate® P (CSL Behring) which contain besides vWF also FVIII, or other plasmatic vWF products or recombinantly manufactured vWF or vWF/FVIII products.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In another preferred embodiment of the use of the von Willebrand Factor or the method of the invention the vWF is used or administered to act as an antidote.

The term "antidote" as used in accordance with the present invention relates to a substance which enhances the diminished function of the thrombocytes. Therefore an antidote according to the invention is not a matter of a classical agonist/antagonist function but improves the function of the thrombocytes which was diminished by substances inhibiting thrombocytes.

In a preferred embodiment of the invention the vWF or the FVIII/vWF are used or administered as a concentrate.

In another preferred embodiment the vWF or the FVIII/vWF has been isolated from human blood plasma or is alternatively administered as a recombinant protein.

In a preferred embodiment of the use of the von Willebrand Factor or the method of the invention the substance inhibiting thrombocytes is selected from the group consisting of a cyclooxygenase inhibitor, an inhibitor of the ADP receptor or a combination thereof. In a more preferred embodiment the cyclooxygenase inhibitor is acetylsalicyl acid and the inhibitor of the ADP receptor is a thienopyridino derivative, preferably clopidogrel or ticlopidine. In the most preferred embodiment the substance inhibiting thrombocytes is acetylsalicylic acid, clopidogrel or the combination acetylsalicylic acid and clopidogrel.

The present invention further related to a composition comprising vWF and a composition comprising FVIII for simultaneous, separate or sequential use for use in the treatment and/or prevention of a bleeding event caused by the administration of substances inhibiting thrombocytes. According to this embodiment the vWF and the FVIII are therefore used or administered in separated standard doses.

The figures show:

Figure 1:
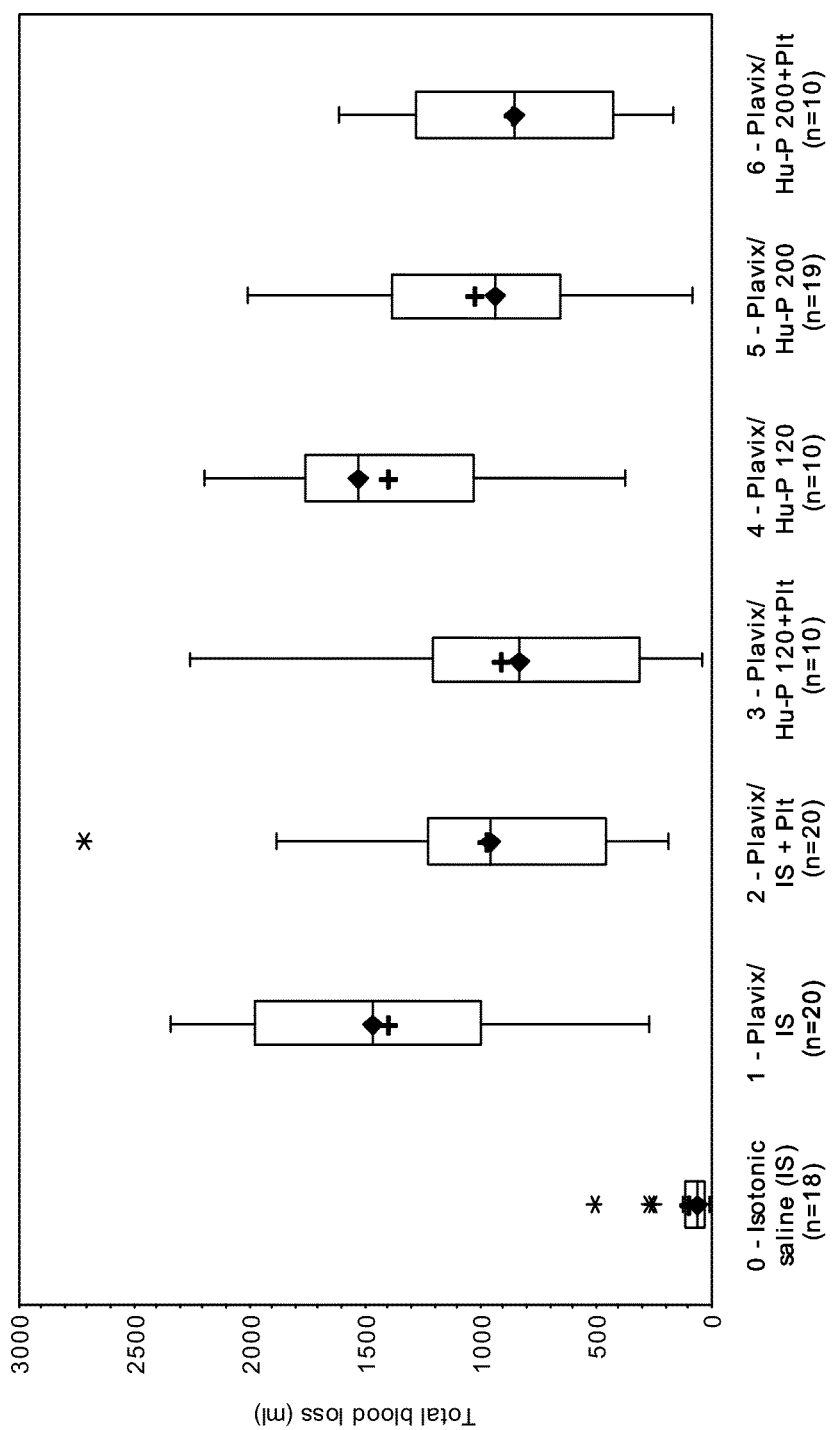
FIG. 1 shows the box plots of total blood loss (significance against group 1 (Plavix® control)) in the rat clopidogrel model.

Without limitation of the present invention the examples illustrate the invention.

EXAMPLE 1

Influence of Transfused Rat Platelets Combined with a vWF and FVIII Concentrate (Haemate® P) on the Bleeding in the Rat Clopidogrel Model Is was investigated whether a dose of 120 and 200 U/kg Haemate® P (i.v.) in combination with freshly prepared rat platelets would reduce the bleeding in clopidogrel treated rats. Two groups of clopidogrel treated rats received Haemate® P (120 and 200 U/kg) without platelets. The study was designed as an open seven-armed trial with 115 rats (+60 platelet donors). The dosing regimen is summarized in table 1.

TABLE 1

Treatment of the groups

| No. | Treatment | Dose/volume/schedule/route | N (f) |
|---|---|---|---|
| 1 | Isotonic saline | —/1.7-2.8 mL/kg b.w./ single injection (t = d 2)/i.v. | 25 |
| | Isotonic saline | —/1 mL/animal/ single injection (t = d 2)/i.v. | |
| 2 | Isotonic saline | —/1.67 mL/kg b.w./ single injection (t = d 2)/i.v. | 25 |
| | Fresh rat platelets | 2.8-3 × 10$^9$/1 mL/animal/ single injection (t = d 2)/i.v. | |
| 3 | Haemate ® P | 120 U/kg/1.67 mL/kg b.w./ single injection (t = d 2)/i.v. | 10 |
| | Fresh rat platelets | 3 × 10$^9$/1 mL/animal/ single injection (t = d 2)/i.v. | |
| 4 | Haemate ® P | 200 U/kg/2.8 mL/kg b.w./ single injection (t = d 2)/i.v. | 15 |
| | Fresh rat platelets | 2.8 × 10$^9$/1 mL/animal/ single injection (t = d 2)/i.v. | |
| 5 | Haemate ® P | 120 U/kg/1.67 mL/kg b.w./ single injection (t = d 2)/i.v. | 10 |
| | Isotonic saline | —/1 mL/animal/ single injection (t = d 2)/i.v. | |
| 6 | Haemate ® P | 200 U/kg/2.8 mL/kg b.w./ single injection (t = d 2)/i.v. | 25 |
| | Isotonic saline | —/1 mL/animal/ single injection (t = d 2)/i.v. | |
| 7 | Negative control for TGA/ no Clopidogrel administration | | 5 |
| | Isotonic saline | 2.8 mL/kg b.w./i.v. | |
| | Isotonic saline | 1 mL/animal/i.v. | |

Rat Platelets

Blood for preparation of the platelet concentrate was taken gently by puncturing the inferior vena cava of donor rats under deep anesthesia. 3.2 mL blood were mixed with 0.8 mL trisodium citrate. Blood samples were pooled and centrifuged at 900 RPM for 30 minutes. Platelet-rich-plasma was collected into a fresh tube and centrifugated at 1800-2000 RPM for 15-17 minutes. The pellet was gently resuspended in Tyrode HEPES+0.3% BSA. Depending on platelet yield animals received 1.6–3×10$^9$ washed platelets intravenous into the tail vein.

Animal Model

Platelet inhibiton/hemorrhage was induced by 2.5 mg/kg clopidogrel (Plavix®) on day 0 and day 1. Tablets were dissolved in isotonic saline and administered by gavage. On day 2 freshly prepared rat platelets were transfused into the tail vein by a bolus. Haemate® P was administered directly prior to platelet transfusion. 15 minutes after administration of platelets, blood loss was determined. The volume of total blood loss was calculated by measuring the HGB present in the saline used for submersion of the tail tip. The tail tip cut was performed with a scalpel knife under deep anesthesia, removing about 3 mm of the tail tip. Immediately upon lesion, the tail tip was submerged in saline, kept at the physiological body temperature of the rats using a water bath. The observation period to monitor bleeding was 30 min.

Bleeding

Figure 2:
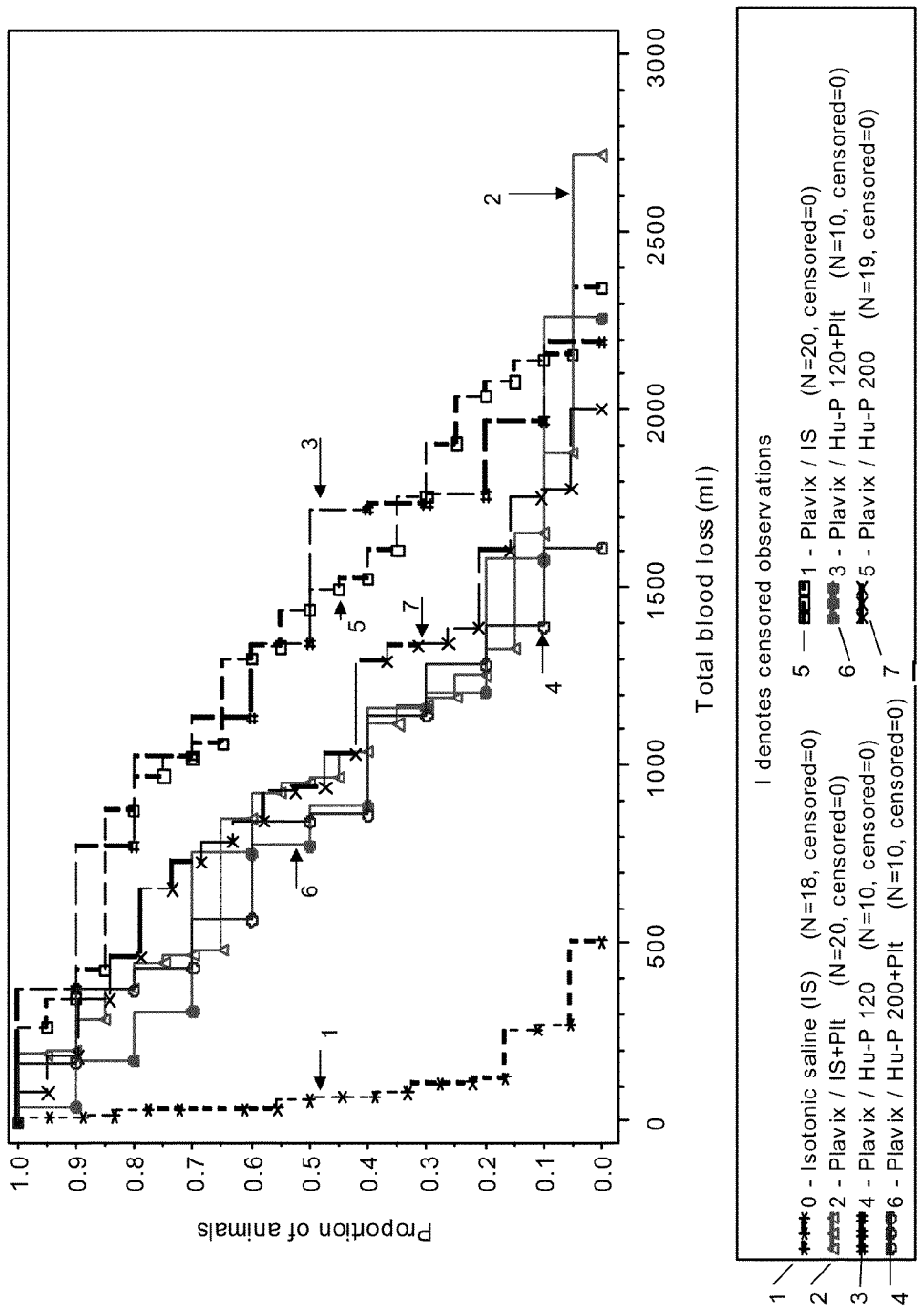
FIG. 2 shows the Kaplan-Meier plot of total blood loss in the rat clopidogrel model.

Blood loss was determined as the total blood loss (t=0-30 min) and analyzed by two-sided exact Wilcoxon test, box plot and Kaplan-Meier plot. Oral treatment with clopidogrel resulted in an increased total blood loss (FIGS. 1 and 2, table 2). FIG. 1 illustrates that total blood loss was significantly reduced in the group receiving platelet transfusion (statistics see table 3). Total blood loss could not be decreased by combination of platelet transfusion and Haemate® P treatment compared to platelets alone. However, monotherapy with Haemate® P resulted in a significant decrease in blood loss in the group that received a dose of 200 U/kg. No influence on blood loss was observed with 120 U/kg.

TABLE 2

Total blood loss (μL)

|  | Group 0 Isotonic saline | Group 1 Plavix/ Isotonic saline | Group 2 Plavix/ Isotonic saline + fresh rat platelets | Group 3 Plavix/ Haemate-P ® 120 U/kg + platelets | Group 4 Plavix/ Haemate-P ® 120 U/kg | Group 5 Plavix/ Haemate-P ® 200 U/kg | Group 6 Plavix/ Haemate-P ® 200 U/kg + platelets |
|---|---|---|---|---|---|---|---|
| N | 18 | 20 | 20 | 10 | 10 | 19 | 10 |
| Mean | 103.9 | 1404.2 | 974.4 | 914.0 | 1403.5 | 1025.6 | 865.9 |
| SD | 125.5 | 624.3 | 626.9 | 676.6 | 573.3 | 553.3 | 483.0 |
| Minimum | 11 | 265 | 189 | 42 | 372 | 81 | 165 |
| Median | 65 | 1466 | 960 | 830 | 1532 | 940 | 852 |
| Maximum | 507 | 2345 | 2716 | 2259 | 2193 | 2002 | 1613 |

TABLE 3

Statistics of total blood loss (exact Wilcoxon test)

| p-value | Group 0 Isotonic saline | Group 1 Plavix/ Isotonic saline | Group 2 Plavix/ Isotonic saline + fresh rat platelets | Group 3 Plavix/ Haemate-P ® 120 U/kg + platelets | Group 4 Plavix/ Haemate-P ® 120 U/kg | Group 5 Plavix/ Haemate-P ® 200 U/kg | Group 6 Plavix/ Haemate-P ® 200 U/kg + platelets |
|---|---|---|---|---|---|---|---|
| Group 0 | — | <0.0001 | <0.0001 | 0.0003 | <0.0001 | <0.0001 | <0.0001 |
| Group 1 | <0.0001 | — | 0.0231 | 0.0529 | 0.9649 | 0.0461 | 0.0278 |
| Group 2 | <0.0001 | 0.0231 | — | 0.6284 | 0.0585 | 0.6940 | 0.7249 |
| Group 3 | 0.0003 | 0.0529 | 0.6284 | — | 0.0821 | 0.4629 | 0.9397 |
| Group 4 | <0.0001 | 0.9649 | 0.0585 | 0.0821 | — | 0.1083 | 0.0494 |
| Group 5 | <0.0001 | 0.0461 | 0.6940 | 0.4629 | 0.1083 | — | 0.4629 |
| Group 6 | <0.0001 | 0.0278 | 0.7249 | 0.9397 | 0.0494 | 0.4629 | — |

Thrombin Generation

Figure 3:
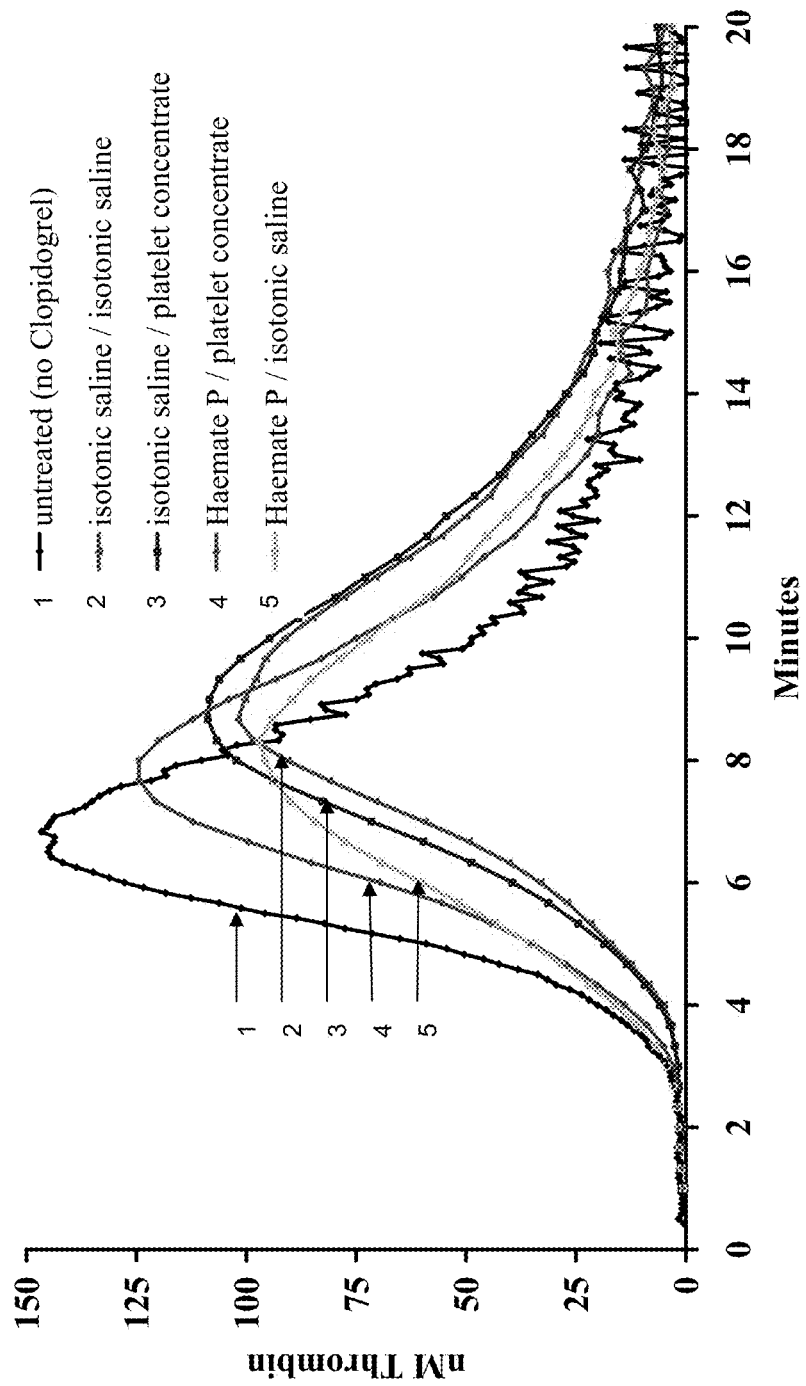
FIG. 3 shows the effect of Haemate® P 200 U/kg and fresh rat platelet concentrate (1.6×109 PLT/animal) on thrombin generation/thrombogram in platelet rich plasma.

Treatment with clopidogrel resulted in a later onset of thrombin formation and in a decrease in peak thrombin (FIG. 3). When Haemate® P was administered to clopigogrel treated rats an earlier onset of thrombin formation was observed but no increase of peak thrombin. Platelet transfusion resulted in an increase in the thrombin peak. Additional or even synergistic effects were seen when platelets and Haemate® P were combined: the peak was increased and the onset of thrombin formation was faster.

EXAMPLE 2

Time Course of Bleeding in Pigs after the Administration of Clopidogrel and Aspirin and after the Additional Infusion of a vWF and FVIII Concentrate (Haemate® P)

Male castrated pigs were administered over a period of three days 75 mg clopidogrel (Plavix®) daily per os via gavage. At the third day acetylsalicylic acid (Aspirin®) was administered intravenously in a dose of 200 mg/kg. 15 minutes later an intravenous bolus of a FVIII/vWF containing concentrate (60 units/kg of FVIII and about 150 units/kg of vWF) were given (treatment group, group 3, n=6). Control animals received an appropriate volume of saline instead of vWF and FVIII concentrate (placebo group, group 2, n=4). 5 animals received neither the thrombocyte inhibitors nor Haemate® P treatment (group 1, negative control). During the experiment the PT and aPTT were determined in plasma, the thromboelastography and the thrombocyte aggregation were performed in whole blood. For the thrombin generation, a test in platelet rich plasma was used.

Figure 6:
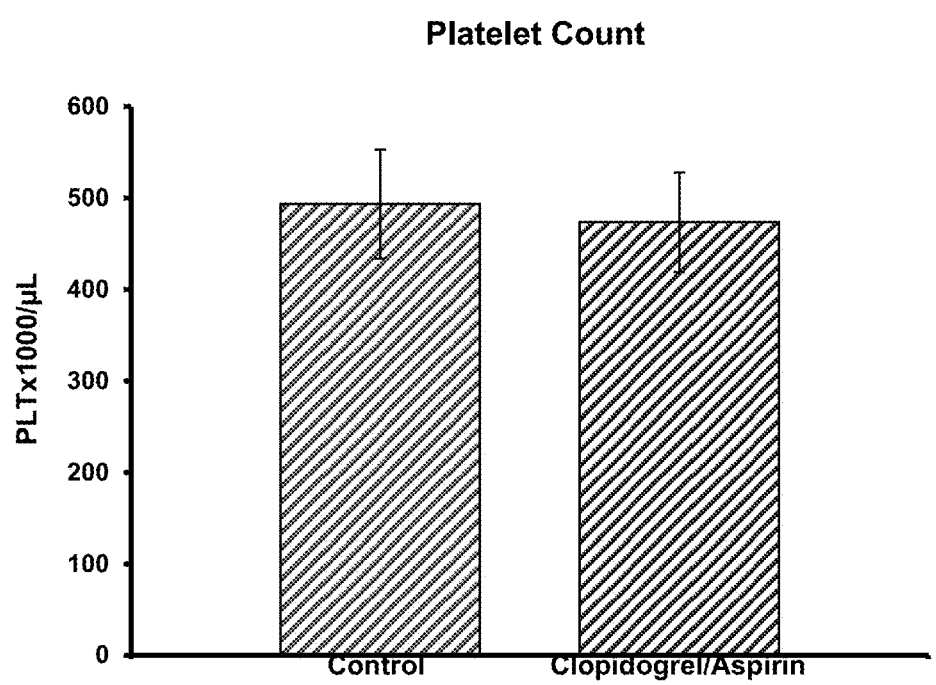
FIG. 6 shows the effect of the administration of Clopidogrel/Aspirin® on platelet count in pigs.

The combined administration of clopidogrel and Aspirin® lead to a thrombocytopathy with impaired platelet aggregation and thrombin generation. After spleen wounding a substantial hemorrhage was caused by the thrombocytopathy. In contrast, the plasmatic coagulation (PT, aPTT) was not influenced by clopidogrel/acetylsalicylic acid treatment. FIG. 6 shows that no significant decrease of the platelet count was observed after the administration of clopidogrel/Aspirin®, thus no thrombocytopenia has been induced.

Figure 4:
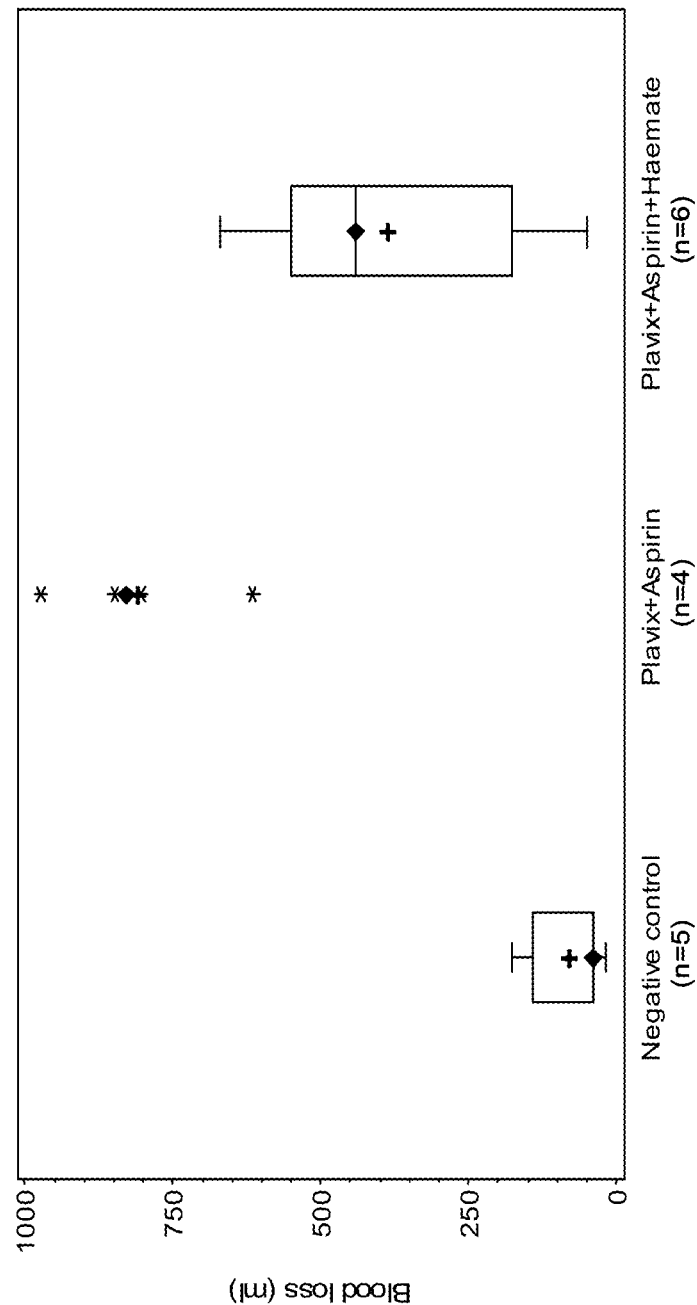
FIG. 4 shows the box plots of blood loss in pigs after the administration of Clopidogrel/Aspirin®.
Figure 5:
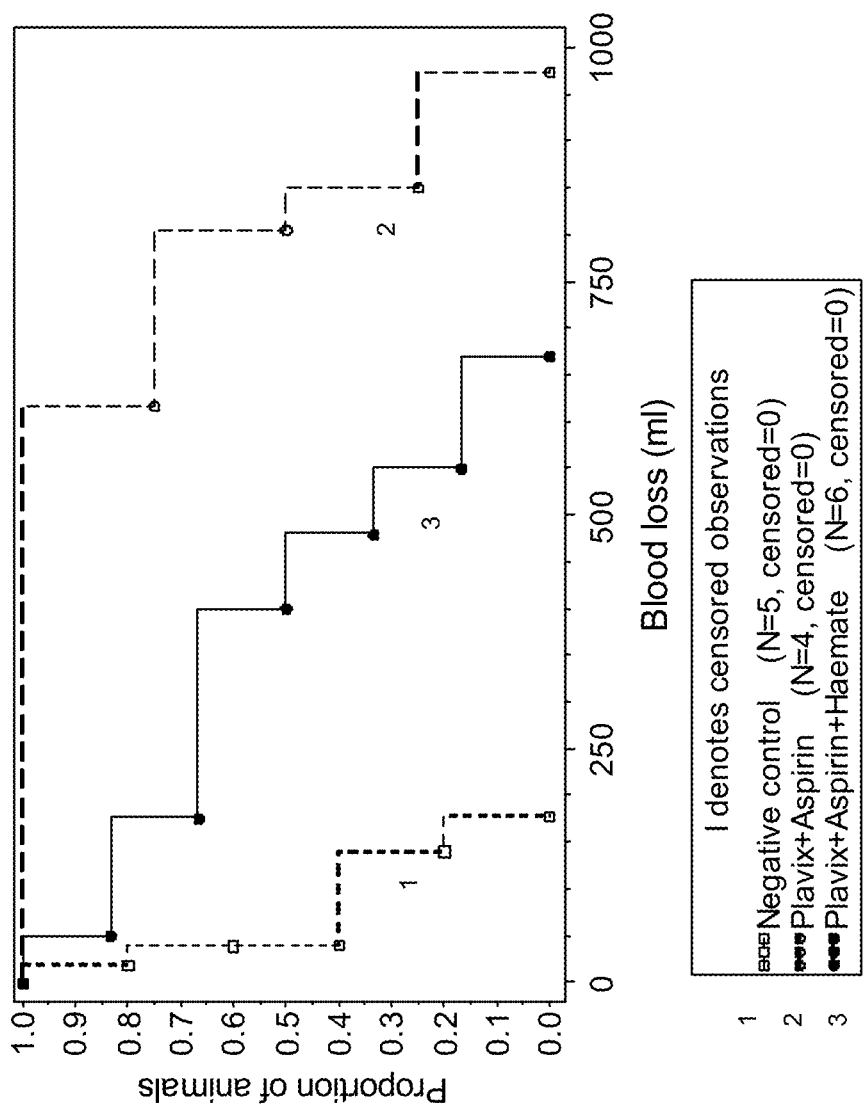
FIG. 5 shows the Kaplan-Meier plot of blood loss in pigs after the administration of Clopidogrel/Aspirin®.

In tables 4 and 5 as well as in FIGS. 4 and 5 it can be seen that in this investigation a treatment with Haemate® P decreased blood loss significantly. It has thus been shown that a concentrate containing a coagulation vWF and factor VIII was able to partly overcome the thrombocyte inhibitor induced thrombocytopathy.

TABLE 4

Blood loss (ml) after Spleen Injury

|  | Group 1 Negative control | Group 2 Placebo group (Plavix/Aspirin + saline) | Group 3 Treatment group Plavix/Aspirin + Haemate ® P |
|---|---|---|---|
| N | 5 | 4 | 6 |
| Mean | 83.2 | 811.3 | 387.7 |
| SD | 71.0 | 148.5 | 233.9 |
| Minimum | 19 | 616 | 50 |

TABLE 4-continued

Blood loss (ml) after Spleen Injury

| | Group 1 Negative control | Group 2 Placebo group (Plavix/Aspirin + saline) | Group 3 Treatment group Plavix/Aspirin + Haemate ® P |
|---|---|---|---|
| Median | 40 | 827.5 | 440 |
| Maximum | 178 | 974 | 670 |

TABLE 5

Statistics of blood loss (Wilcoxon test)

| Comparison | p-value |
|---|---|
| Negative control (Group 1) - Placebo group (Group 2) | 0.0143 |
| Negative control (Group 1) - Treatment group (Group 3) | 0.0285 |
| Placebo group (Group 2) - Treatment group (Group 3) | 0.0190 |

The invention claimed is:

1. A method of treating and/or preventing a bleeding event associated with a thrombopathy, comprising administering to an individual in need thereof an effective amount of a composition before, at the same time as, or after administering to the individual at least one substance inhibiting thrombocytes, wherein the thrombopathy is induced by the at least one substance inhibiting thrombocytes in the individual, wherein the at least one substance comprises an ADP receptor inhibitor, and wherein the composition consists of
   (a) von-Willebrand-Factor (vWF), or
   (b) vWF and Factor VIII (FVIII),
   alone or in combination with one or more diluent, excipient, carrier, preservative, buffer, solvent, stabilizer, and/or additive.

2. The method of claim 1, wherein the at least one substance inhibiting thrombocytes comprises an ADP receptor inhibitor and a cyclooxygenase inhibitor.

3. The method of claim 2, wherein the cyclooxygenase inhibitor is acetylsalicylic acid.

4. The method of claim 1, wherein the ADP receptor inhibitor is a thienopyridino derivative, clopidogrel, or ticlopidine.

5. The method of claim 1, wherein the composition consisting of vWF or vWF and FVIII, alone or in combination with one or more diluent, excipient, carrier, preservative, buffer, solvent, stabilizer, and/or additive, is administered as an antidote.

6. The method of claim 1, wherein the composition consisting of vWF or vWF and FVIII, alone or in combination with one or more diluent, excipient, carrier, preservative, buffer, solvent, stabilizer, and/or additive, is administered as a concentrate.

7. The method of claim 1, wherein the vWF has been isolated from human blood plasma.

8. The method of claim 1, wherein the vWF is recombinant.

9. The method of claim 1, wherein the vWF is administered to the individual at a dose of 10 to 1000 units per kg body weight.

10. The method of claim 1, wherein the vWF is administered to the individual at a dose of 30 to 500 units per kg body weight.

11. The method of claim 1, wherein the vWF is administered to the individual at a dose of 10 to 1000 units per kg body weight and the FVIII is administered to the individual at a dose of 5 to 400 units per kg body weight.

12. The method of claim 1, wherein the vWF is administered to the individual at a dose of 30 to 500 units per kg body weight and the FVIII is administered to the individual at a dose of 20 to 200 units per kg body weight.

13. The method of claim 1, wherein at least one of the vWF and the FVIII has been isolated from human blood plasma.

14. The method of claim 1, wherein at least one of the vWF and the FVIII is recombinant.

15. The method of claim 1, wherein the composition consists of vWF and FVIII, alone or in combination with one or more diluent, excipient, carrier, preservative, buffer, solvent, stabilizer, and/or additive.

16. The method of claim 1, wherein the ADP receptor inhibitor is clopidogrel.

17. The method of claim 1, wherein the ADP receptor inhibitor is ticlopidine.

18. The method of claim 1, wherein the at least one substance inhibiting thrombocytes comprises an ADP receptor inhibitor and a cyclooxygenase inhibitor, and wherein the ADP receptor inhibitor is ticlopidine and the cyclooxygenase inhibitor is acetylsalicylic acid.

19. The method of claim 1, wherein the at least one substance inhibiting thrombocytes comprises an ADP receptor inhibitor and a cyclooxygenase inhibitor, and wherein the ADP receptor inhibitor is clopidogrel and the cyclooxygenase inhibitor is acetylsalicylic acid.

20. The method of claim 1, wherein the method consists of administering to the individual in need thereof an effective amount of the composition before, at the same time as, or after administering the at least one substance inhibiting thrombocytes.

* * * * *